United States Patent
Ye

(10) Patent No.: US 6,521,418 B1
(45) Date of Patent: Feb. 18, 2003

(54) G PROTEIN-COUPLED RECEPTOR WITH AN ENLARGED EXTRACELLULAR DOMAIN

(75) Inventor: Richard D. Ye, Willowbrook, IL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/117,440

(22) PCT Filed: Jan. 30, 1997

(86) PCT No.: PCT/US97/01736

§ 371 (c)(1),
(2), (4) Date: Jul. 28, 1998

(87) PCT Pub. No.: WO97/28188

PCT Pub. Date: Aug. 7, 1997

(51) Int. Cl.$^7$ ............ C12N 15/00; C12N 5/00; C12N 1/20; C12N 15/63; C07H 21/04
(52) U.S. Cl. ............ 435/69.1; 435/170; 435/171; 435/455; 435/471; 435/325; 435/252.3; 435/254.11; 435/320.11; 536/23.1; 536/23.5; 536/24.31
(58) Field of Search ............... 536/23.1, 24.31, 536/25.5, 23.5; 530/350; 435/69.1, 170, 171, 455, 471, 325, 252.3, 254.11, 320.11

(56) References Cited

PUBLICATIONS

Ye, et al., The rabbit neutrophil N–formyl peptide receptor, 1993, *J. Immunology*, 150(4):1383–1394.
Probst, et al., Review article: Sequence alignment of the G–protein coupled receptor superfamily, 1992, *DNA and Cell Biology*, 11(1):1–20.
Ausebel, et al., Expression and purification of maltose–binding protein fusions, 1990, *Current Protocols in Molecular Biology*, New York: Green Publishing Associates and Wiley– Interscience, 2:16.6.1–16.6.12.
Ausebel, et al., Expression and purification of glutathione–S–transferase fusion proteins, 1990, *Current Protocols in Molecular Biology*, New York: Green Publishing Associates and Wiley–Interscience, 2:16.7.1–16.7.8.
Boulay et al, "The Human N–Formylpeptide Receptor. Characterization of Two cDNA Isolates . . . ", Biochemistry, vol. 29, No. 50, pp. 11123–11133, Dec. 1990.*
Ames et al, "Molecular Cloning and Characterization of the Human Anaphylatoxin C3a Receptor." J. of Biological Chemistry, vol. 271, No. 34, pp. 20231–20234, Aug. 1996.*
Crass et al, "Expression cloning of the human C3a anaphylatoxin receptor from differentiated U–937 cells." Eur. J. Immunology, vol. 26, No. 8, pp. 1944–1950, 1996.*
Roglic et al, "cDNA cloning of a novel G protein–coupled receptor with a large extracellular loop structure." Biochimica et Biophysica Acta, vol. 1305, No. (1–2), pp. 39–43, 1996.*
Rothmann et al, "Heart muscle–specific gene expression using replication defective recombinant adenovirus", Gene Therapy, vol 3, No. 10, pp. 919–926, 1996.*
Feng et al, "HIV–1 entry cofactor: Functional cDNA cloning of a seven–transmembrane, G protein–coupled receptor.", Science, vol. 272, No. 5270, pp. 1955–1958, 1996.*

* cited by examiner

Primary Examiner—Anthony C. Caputa
Assistant Examiner—Karen A. Canella
(74) Attorney, Agent, or Firm—Emily Holmes; Thomas Fitting

(57) ABSTRACT

The invention features a G protein-coupled receptor that has an enlarged extracellular loop between the fourth and fifth transmembrane domains. A nucleic acid encoding the receptor was isolated from a human granulocytic cell library and antibodies generated against the polypeptide revealed expression in a variety of tissues including heart, placenta, and lung. This antibody, or others that specifically bind the G protein-coupled receptor of the invention, can be used in the diagnosis of diseases or conditions that are associated with upregulation of the receptor, as occurs, for example, when hematopoietic cells differentiate. These diseases include inflammatory and neurological diseases, particularly Alzheimer's Disease. The nucleic acids, polypeptides, and antibodies described herein can also be used as therapeutic agents to treat these diseases by inhibiting the expression or activity of the receptor. They can also be used in the treatment of obesity.

17 Claims, 6 Drawing Sheets

```
                                                              -81
                                                               -1
GGTGGGGACCAGAGACTCGTGGAGACATCCAGGTGCTGAAGCCTTCAGCTACTGTCTCAGTTTTTGAAGTTTAGCA

ATG GCG TCT TTC TCT GCT GAG ACC AAT TCA ACT GAC CTA CTC TCA CAG CCA TGG AAT GAG    60
MET Ala Ser Phe Ser Ala Glu Thr Asn Ser Thr Asp Leu Leu Ser Gln Pro Trp Asn Glu    20

CCC CCA GTA ATT CTC TCC ATG GTC ATT CTC AGC CTT ACT TTT TTA CTG GGA TTG CCA GGC   120
Pro Pro Val Ile Leu Ser Met Val Ile Leu Ser Leu Thr Phe Leu Leu Gly Leu Pro Gly    40

AAT GGG CTG GTG CTG TGG GCT GGC GTG ACA ATG CAG ACA CGG ACA GTG AAC ACA ATT TGG   180
Asn Gly Leu Val Leu Trp Ala Gly Val Thr Met Gln Thr Arg Thr Val Asn Thr Ile Trp    60

TTC CTC CAC CTC ACC TTG GCG GAC CTC TCC CTG CTC TGC TGC CTC TCC CCC TTC CTG GCT   240
Phe Leu His Leu Thr Leu Ala Asp Leu Ser Leu Leu Cys Cys Leu Ser Leu Pro Phe Ser    80

CAC TTG GCT CTC CAG GGA CAG TGG CCC TAC GGC AGG TTC CTA TGC AAG CTC ATC CCC TCC   300
His Leu Ala Leu Gln Gly Gln Trp Pro Tyr Gly Arg Phe Leu Cys Lys Leu Ile Pro Ser   100

ATC ATT GTC CTC AAC ATG TTT GCC AGT GTC TTC CTC CTT ACT GCC ATT AGC CTG GAT CGC   360
Ile Ile Val Leu Asn Met Phe Ala Ser Val Phe Leu Leu Thr Ala Ile Ser Leu Asp Arg   120

TGT CTT GTA TTC AAG CCA ATC TGG TGT CAG AAT CAT CGC AAT GTA GGG ATG GCC TGC        420
Cys Leu Val Phe Lys Pro Ile Trp Cys Gln Asn His Arg Asn Val Gly Met Ala Cys       140

TCT ATC TGT GGA TGT ATC TGG GTG GTG GCT TTT GTG ATG TGC ATT CCT GTG TTC GTG TAC   480
Ser Ile Cys Gly Cys Ile Trp Val Val Ala Phe Val Met Cys Ile Pro Val Phe Val Tyr   160
```

FIG. 1A

```
CGG GAA ATC TTC ACT ACA GAC AAC CAT AAT AGA TGT GGC TAC AAA TTT GGT CTC TCC AGC   540
Arg Glu Ile Phe Thr Thr Asp Asn His Asn Arg Cys Gly Tyr Lys Phe Gly Leu Ser Ser   180

TCA TTA GAT TAT CCA GAC TTT TAT GGA GAT CCA GGA GAA CTA AAC AGG TCT CTT GAA AAC ATT   600
Ser Leu Asp Tyr Pro Asp Phe Tyr Gly Asp Pro Gly Glu Leu Asn Arg Ser Leu Glu Asn Ile   200

GTT CAG CGG CCT GGA GAA ATG CGG AAT GAT AGG TTA CGA AGG CCT TCC TCT TTC CAA ACA AAT GAT   660
Val Gln Arg Pro Gly Glu Met Arg Asn Asp Arg Leu Arg Arg Pro Ser Ser Phe Gln Thr Asn Asp   220

CAT CCT TGG ACA GTC CCC ACT GTC TTC CAA CCT CAA ACA TTT CAA AGA CCT TCT GCA GAT   720
His Pro Trp Thr Val Pro Thr Val Phe Gln Pro Gln Thr Phe Gln Arg Pro Ser Ala Asp   240

TCA CCT CCT AGG GGT TCT GCT AGG TTA ACA AGT CAA CTG TAT TCT AAT GTA TTT AAA   780
Ser Leu Pro Arg Gly Ser Ala Arg Leu Thr Ser Gln Leu Tyr Ser Asn Val Phe Lys   260

CCT GCT GAT GTG GTC TCA CCT AAA ATC CCC AGT GGG TTT CCT ATT GAA GAT CAC GAA ACC   840
Pro Ala Asp Val Val Ser Pro Lys Ile Pro Ser Gly Phe Pro Ile Glu Asp His Glu Thr   280

AGC CCA CTG GAT AAC CTG TCT GAT GCT TTT CTC TCT ACT CAT TTA AAG CTG TTC CCT AGC GCT   900
Ser Pro Leu Asp Asn Leu Ser Asp Ala Phe Leu Ser Thr His Leu Lys Leu Phe Pro Ser Ala   300

TCT AGC AAT TCC TTC TAC GAG TCT TAC CTA CCA CAA GGT TTC CAG GAT TAT TAC AAT TTA   960
Ser Ser Asn Ser Phe Tyr Glu Ser Tyr Leu Pro Gln Gly Phe Gln Asp Tyr Tyr Asn Leu   320

GGC CAA TTC ACA GAT GAC GAT CAA GTG CCA ACA CCC CTC GTG GCA ATA ACG ATC ACT AGG   1020
Gly Gln Phe Thr Asp Asp Asp Gln Val Pro Thr Pro Leu Val Ala Ile Thr Ile Thr Arg   340

CTA GTG GTG GGT TTC CTG GGT TTC CTG CCC TCT GTT ATC ATG ATA GCC TGT TAC AGC TTC ATT GTC   1080
Leu Val Val Gly Phe Leu Pro Ser Val Ile Met Ile Ala Cys Tyr Ser Phe Ile Val   360
```

FIG. 1B

```
TTC CGA ATG CAA AGG GGC CGC TTC GCC AAG TCT CAG AGC AAA ACC TTT CGA GTG GCC GTG  1140
Phe Arg Met Gln Arg Gly Arg Phe Ala Lys Ser Gln Ser Lys Thr Phe Arg Val Ala Val   380

GTG GTG GCT GTC TTT CTT GTC TGC TGG ACT CCA TAC CAC ATT TTT GGA GTC CTG TCA       1200
Val Val Ala Val Phe Leu Val Cys Trp Thr Pro Tyr His Ile Phe Gly Val Leu Ser       400

TTG CTT ACT GAC CCA GAA ACT CCC TTG GGG AAA ACT CTG ATG TCC GAT CAT GTA TGC       1260
Leu Leu Thr Asp Pro Glu Thr Pro Leu Gly Lys Thr Leu Met Ser Asp His Val Cys       420

ATT GCT CTA GCA TCT GCC AAT AGT TGC TTT AAT CCC TTC TTT TAT GCC CTC TTG GGG AAA   1320
Ile Ala Leu Ala Ser Ala Asn Ser Cys Phe Asn Pro Phe Phe Tyr Ala Leu Leu Gly Lys   440

GAT TTT AGG AAG AAA GCA AGG CAG ATT CAG ATC GGG ATT CTG GAG GCA GCC TTC AGT GAG   1380
Asp Phe Arg Lys Lys Ala Arg Gln Ile Gln Ser Ile Gly Ile Leu Glu Ala Ala Phe Ser Glu 460

GAG CTC ACA CGT TCC ACC CAC TGT CCC TCA AAC AAT GTC ATT TCA GAA AGA AAT AGT ACA   1440
Glu Leu Thr Arg Ser Thr His Cys Pro Ser Asn Asn Val Ile Ser Glu Arg Asn Ser Thr   480

ACT GTG TGA AAA TGT GGA GCA GCC AAC AAG GGG CTC TTA GGC AAT CAC ATA GTG AAA       1500
Thr Val END                                                                        482

GTTTATAAGAGGATGAAGTGATATGGTGAGCAGCGGACTTCAAAAACTGTCAAAGAATCAATCCAGCGGTTCTCAAACGG  1580
TACACAGACTATTGACATCAGCATCACCTAGCATCACCCAGCAGAAACTTGTTAGAAATGCAAATTCTCAAGCCGCATCC  1660
TCGGAATCTCTCTGGGGTGGACCCCAGCAAGGCCACTTAACAACAACCCTCGTTTCTGATTAATGCTAAATGTAAGAATCAT 1740
TGTAAACATTAGTTCTATTCTATCCGAAACTATGTGAAATAAGAAGCTACTTGTTTTTAAATGATGTTGAA           1820
TATTTGTCGATATTTCCATCATTAAATTTTTCCTTAGCATTGTCTAAGTCTTCCAAAAAAAAAAAAA              1889
```

FIG. 1C

G PROTEIN-COUPLED RECEPTOR WITH AN ENLARGED EXTRACELLULAR DOMAIN

This work was supported in part by a grant from the National Institutes of Health (GM46572). The government therefore has certain rights in the invention.

BACKGROUND OF THE INVENTION

The field of the invention is G protein-coupled receptors.

The rhodopsin-like G protein-coupled receptors, which are the single largest class of cell surface receptors, mediate a wide variety of essential physiological functions. For example, G protein-coupled receptors mediate the chemotactic movement of cells that ensures an adequate immune response, transmit the signals carried by hormones, and capture external stimuli such as the photons that strike the retina and the odorant molecules that strike the nasal epithelium (Probst et al., DNA Cell Biol. 11:1–20, 1992). All G protein-coupled receptors contain seven domains that traverse back and forth across the cell membrane; the proteinaceous loops that form between these transmembrane domains extend into the extracellular and intracellular spaces. The loops that extend extracellularly specifically interact with ligands, particularly peptide and protein ligands, and the intracellular loops interact with G proteins on the inner surface of the cell membrane, thereby beginning the biochemical cascade that transmits the extracellular signal to the interior of the cell. The third intracellular loop of many G protein-coupled receptors, particularly those that function as adrenergic and cholinergic receptors, is the largest intracellular structure, and is thought to be especially important for the interaction between the receptor and a G protein (Lefkowitz et al., Cold Spring Harbor Symposia Quant. Biol. 53:507–514, 1988).

SUMMARY OF THE INVENTION

The invention features a G protein-coupled receptor that has an enlarged extracellular loop between the fourth and fifth transmembrane domains. A nucleic acid encoding the receptor was isolated from a human granulocytic cell library and antibodies generated against the polypeptide revealed expression in a variety of tissues including heart, placenta, and lung. This antibody, or others that specifically bind the G protein-coupled receptor of the invention, can be used in the diagnosis of diseases or conditions that are associated with upregulation of the receptor, as occurs, for example, when hematopoietic cells differentiate. These diseases include inflammatory and neurological diseases, such as Alzheimer's Disease. The nucleic acids, polypeptides, and antibodies described herein can also be used as therapeutic agents to treat these diseases by inhibiting the expression or activity of the receptor. They can also be used in the treatment of obesity.

Other features and advantages of the invention will be apparent from the detailed description and from the claims. Although materials and methods similar or equivalent to those described herein can be used in the practice or testing of the invention, the preferred materials and methods are described below.

BRIEF DESCRIPTION OF THE DRAWING

FIG. 1 is a representation of the nucleotide (top line; SEQ ID NO: 1) and deduced amino acid (bottom line; SEQ ID NO:2) sequence of the AZ3B cDNA clone. The nucleotide sequence is positively numbered from the first initiation codon (ATG) of the longest open reading frame; 5' untranslated sequence is numbered negatively. Putative transmembrane domains are shaded, and predicted N-glycosylation sites are marked with circles.

In FIG. 4A, AZ3B mRNA (Poly($A^+$)) is analyzed in eight different human tissues. In FIG. 4B, total AZ3B RNA is analyzed in undifferentiated and differentiated HL-60 cells.

DETAILED DESCRIPTION

Figure 2:
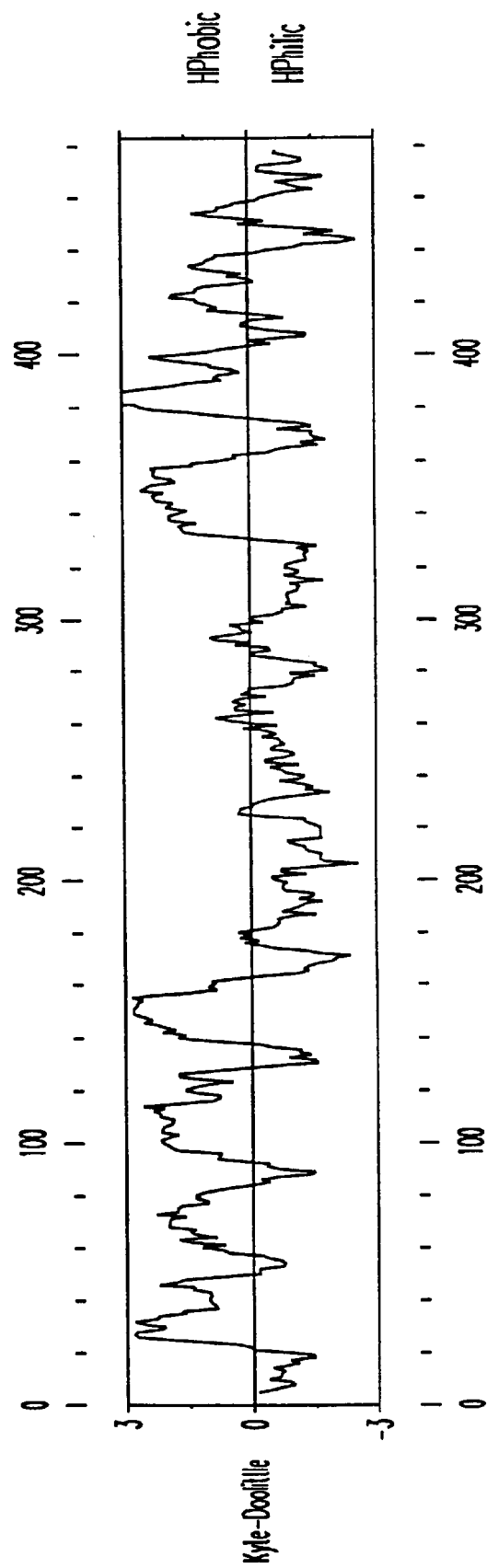
FIG. 2 is a hydropathy plot generated using the AZ3B protein sequence. The hydrophobicity index is shown above the horizontal line, and the hydrophilicity index is shown below the line.

As stated above (and further described in the Examples, below), the invention provides isolated nucleic acids that encode a G protein-coupled receptor having an enlarged extracellular loop between the fourth and fifth transmembrane domains, as well as fragments thereof (for example, see the nucleic acid of FIG. 1 (SEQ ID NO:1). By "enlarged extracellular loop" is meant a loop that is larger than the comparable extracellular loop of known G protein-coupled receptors. Preferably, the enlarged loop consists of at least 50 amino acid residues, more preferably of at least 100 amino acid residues, and most preferably, of at least 160 amino acid residues. A preferred fragment of the nucleic acid will encode all or part of the enlarged extracellular loop (for.example, see nucleotides 481–996 of FIG. 1). The nucleic acids of the invention can contain naturally occurring sequences (as in FIG. 1), or sequences that differ from those that occur naturally, but, due to the degeneracy of the genetic code, encode the same polypeptide (for example, the polypeptide of SEQ ID NO:2). These nucleic acids can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid can be double-stranded or single-stranded (i.e., either a sense or an anti-sense strand).

By "isolated nucleic acid" is meant a nucleic acid that is separated from either the 5' or the 3' coding sequence with which it is immediately contiguous in the naturally occurring genome of an organism. The nucleic acid is not limited to sequences that encode polypeptides; some or all of the non-coding sequences that lie upstream or downstream from a coding sequence can also be included. These isolated nucleic acids can be, for example, cDNA or genomic DNA fragments that were produced by the polymerase chain reaction (PCR) or generated by treatment with restriction endonuclesase, or a ribonucleic acid (RNA) fragment produced by in vitro transcription.

The isolated nucleic acids of the invention are not limited to those which are naturally occurring, and thus may include fragments not found as such in the natural state. Thus, the invention encompasses recombinant molecules, such as those in which a nucleic acid sequence (for example, the sequence of AZ3B) is incorporated into a vector (for example, a plasmid or viral vector) or into the genome of a heterologous cell (or the genome of a homologous cell, at a position other than the natural chromosomal location). Similarly, the nucleic acid can form part of a hybrid gene encoding additional polypeptide sequences (for example, sequences that function as a "marker" or "reporter") that can be used, for example, to produce a fusion protein. Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter.

Detecting Nucleic Acids that Hybridize with AZ3B cDNA

The AZ3B cDNA sequence described above can be used to detect and isolate additional nucleic acids with which it will hybridize. These nucleic acids include, for example, nucleic acids that encode homologous receptors in other species, splice variants of the AZ3B sequence in humans or other mammals, or related nucleic acids that, by encoding a G protein-coupled receptor with an enlarged extracellular loop between the fourth and fifth transmembrane domains, would be classified as members of this new receptor family. Accordingly, the invention features methods of detecting and isolating these nucleic acids. In these methods, a sample (for example, a nucleic acid library, such as a cDNA or genomic library) is contacted (or "screened") with an AZ3B-specific probe (for example, a fragment of SEQ ID NO:1 that is at least 12 nucleotides long). The probe will selectively hybridize to nucleic acids encoding related polypeptides (or to complementary sequences therof). Because the polypeptide encoded by AZ3B is related to other G protein-coupled receptors (all, for example contain seven transmembrane domains), the term "selectively hybridize" is used to refer to an event in which a probe binds to nucleic acids encoding G protein-coupled receptors that have an enlarged extracellular loop (or to complementary sequences thereof) to a detectably greater extent than to nucleic acids encoding G protein-coupled receptors that do not have this characteristic feature, (or to complementary sequences thereof). Preferably, the probe is an "AZ3B-specific probe" and encompasses nucleic acids that can bind to nucleic acids encoding G protein-coupled receptors with an enlarged extracellular loop (or to complementary sequences thereof).

The discovery of the AZ3B cDNA allows, for the first time, production of nucleic acid probes that specifically hybridize with nucleic acids that encode G protein-coupled receptors within the AZ3B family. The probes, which can contain at least 12 (for example, 15, 25, 50, 100, or 200 nucleotides) can be produced using any of several standard methods (see, for example, Ausubel et al., supra). For example, the probes can be generated using PCR amplification methods; primers can be designed that amplify an AZ3B-specific nucleic acid (for example, a nucleic acid in the enlarged extracellular loop) that can be used as a probe to screen a nucleic acid library, as described above, and thereby detect nucleic acids (within the library) that hybridize to the probe.

One single-stranded nucleic acid is said to "selectively hybridize" to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing an equivalent or lower salt concentration as the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2X SSC is 10-fold more concentration than 0.2X SSC). Nucleic acids are hybridized at 42° C. in 2X SSC/0.1% SDS (sodium dodecylsulfate; a detergent) and then washed in 0.2X SSC/0.1% SDS at room temperature (for conditions of low stringency); 0.2X SSC/0.1% SDS at 42° C. (for conditions of moderate stringency); and 0.1X SSC at 68° C. (for conditions of high stringency). Washing can be carried out using only one of the conditions given, or each of the conditions can be used (for example, washing for 10–15 minutes each in the order listed above. Any or all of the washes can be repeated. As mentioned above, optimal conditions will vary and can be determined empirically.

The nucleic acids hybridized can be obtained from any biological cell, such as the cell of a mammal. Thus, the nucleic acids detected using, for example, the AZ3B cDNA sequence, can be those of a human, mouse, rat, guinea pig, cow, sheep, horse, pig, rabbit, monkey, dog, or cat.

Once detected, the nucleic acids can be isolated by any of a number of standard techniques (see, for example, Sambrook et al., Molecular Cloning, A Laboratory Manual, 2nd Ed. Cold Spring Harbor Laboratory Press, Cold Spring Harbor, N.Y., 1989).

The nucleic acids described above can also be used as probes to identify biological tissues or cells that express genes encoding the G protein-coupled receptor of the invention. Cells that express this receptor can be identified by standard techniques, such as Northern blot or RNAse Protection analyses. Gene expression can be more precisely localized to particular cells within a tissue by performing in situ hybridization. Expression of these nucleic acids can be used to diagnose neurological diseases, particularly Alzheimer's Disease, and inflammatory diseases such as asthma, chronic obstructive pulmonary disease, cystic fibrosis, sinusitis, rhinitis, atherosclerosis, glomerulonephritis, multiple sclerosis, psoriasis, or inflammatory bowel disease.

Expression of Az3B and AZ3B-like Gene Products

The nucleic acids of the invention can be inserted into vectors, such as plasmid or viral vectors, which will facilitate expression of the insert. The expressed polypeptide can be used directly as a therapeutic agent, or it can be used to generate antibodies that, in turn, are therapeutically useful. Accordingly, expression vectors containing the nucleic acid of the invention, cells transfected with these vectors, the polypeptides expressed, and antibodies generated, against either the entire polypeptide or an antigenic fragment thereof, are among the preferred embodiments.

Thus, as used herein, the term "transfected cell" means any cell into which (or into an ancestor of which) has been introduced, by means of recombinant DNA techniques, a nucleic acid encoding an AZ3B-like polypeptide, i.e., a G protein-coupled receptor having an enlarged extracellular loop between the fourth and fifth transmembrane domains.

As is well known in the art, transfection can be mediated by expression vectors that contain regulatory elements such as promotors and/or enhancers, which facilitate transcription of the inserted nucleic acid in the cell, origins of replication, and other genes, such as the neomycin-resistance gene, which encodes a selectable marker that imparts G418 resistance to cells in which it is expressed, and thus permits phenotypic selection of the transfected cells. Those of skill in the art could readily determine whether a regulatory element is suitable for use in any given experimental context.

In general, the polypeptides of the invention can be produced by transfecting suitable host cells with the corresponding cDNA in a suitable expression vehicle. Any of a wide variety of expression systems may be used; the precise host cell is not critical. For example, G protein-coupled receptors, such as the receptor encoded by AZ3B, can be produced in a prokaryotic host, such as the bacterium *E. coli*, or in a eukaryotic host, such as an insect cell (for example, Sf21 cells), or mammalian cells (e.g., COS cells, NIH 3T3 cells, or HeLa cells). These cells are available from many sources, including the American Type Culture Collection (Rockville, Md.).

Transfection methods are described by Ausubel et al. (Current Protocols in Molecular Biology, John Wiley & Sons, New York, N.Y., 1994), and expression vehicles may be chosen from those widely known, such as those described in Cloning Vectors: A Laboratory Manual (P. H. Pouwels et al., 1985, Supp. 1987).

Vectors suitable for use in the present invention include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example the expression vector pBacPAK9 from Clontech, Palo Alto, Calif.) for use in insect cells. The nucleic acids in such vectors are operably linked to a promoter, which is selected based on, for example, the cell type in which expression is sought. For example, a T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are available. These promotors are so named for their ability to direct expression of a nucleic acid in a given tissue or cell type within the body. Skilled artisans are well aware of numerous promoters and other regulatory elements which can be used to direct expression of nucleic acids.

Viral vectors that can be used in the invention include, for example, retroviral, adenoviral and adeno-associated vectors, herpes virus, simian virus 40 (SV40), and bovine papilloma virus vectors (see, for example, Gluzman (Ed.), Eukaryotic Viral Vectors, Cold Spring Harbor Laboratory Press, Cold Spring Harbor, N.Y.). Preferably, the virus is a retrovirus.

As used herein, both "protein" and "polypeptide" mean any chain of amino acid residues, regardless of length or post-translational modification (e.g., glycosylation or phosphorylation). The polypeptides of the invention are referred to as "substantially pure," meaning that they are at least 60% by weight (dry weight) the polypeptide of interest, e.g., a polypeptide containing the AZ3B amino acid sequence. Preferably, the polypeptide is at least 75%, more preferably at least 90%, and most preferably at least 99%, by weight, the polypeptide of interest. Purity can be measured by any appropriate standard method, e.g., column chromatography, polyacrylamide gel electrophoresis, or HPLC analysis. The polypeptide can be a naturally occurring, synthetic, or recombinant molecule consisting of a hybrid with one portion, for example, being encoded by all or part of the AZ3B nucleic acid molecule, and a second portion being encoded by all or part of a second gene. For example, the AZ3B polypeptide may be fused to a hexahistidine tag to facilitate purification of bacterially expressed protein, or to a hemagglutinin tag to facilitate purification of protein expressed in eukaryotic cells.

The polypeptides of the invention can also be chemically synthesized (this approach may be limited to polypeptides that constitute a small fragment of the G protein-coupled receptor), or they can be purified from tissues in which they are naturally expressed, according to standard biochemical methods of purification.

Also included in the invention are "functional polypeptides," which possess one or more of the biological functions or activities of the G protein-coupled receptor of the invention. These functions or activities are described in detail below and encompass biologic, morphologic, or phenotypic alterations in the cell. A functional polypeptide is also considered within the scope of the invention if it serves as an immunogen for production of antibodies that specifically bind to the receptor. It is well within the abilities of skilled artisans to determine whether a polypeptide, regardless of size, retains a function or activity of the G protein-coupled receptor of the invention. The functional polypeptides may contain modification of the primary amino acid sequence. Preferably these modifications consist of conservative amino acid substitutions. A sequence that contains conservative amino acid substitutions will differ from SEQ ID NO:2 only by substitutions of one amino acid for another of the same class (for example, substitution of one hydrophobic amino acid, such as isoleucine, valine, leucine, or methionine, for another; substitution of one polar amino acid for another, such as substitution of arginine for lysine, glutamic acid for aspartic acid, or glutamine for asparagine). Substitutions may be the result of deliberate manipulation of the sequence, for example by site-directed mutagenesis, or may arise spontaneously. Also encompassed are additions or deletions of amino acid residues and non-conservative amino acid substitutions, provided that the polypeptide retains at least one activity or epitope that is specific to the G protein-coupled receptor of the invention. For example, polypeptides in which one or more amino acid residues have been deleted from SEQ ID NO:2 are encompassed as long as, for example, the polypeptide mediates release of histamine from basophils or mast cells to a degree that is comparable to the full-length polypeptide. The overall size of the polypeptide is irrelevant.

Production of Antibodies

Antibodies, such as those contained in the rabbit and mouse antisera described above ("polyclonal antibodies") are also within the scope of the invention To generate antibodies that will specifically bind the G protein-coupled receptor of the invention, full-length sequences encoding the receptor, or a portion of the sequence thereof, can be expressed as C-terminal fusion molecules with glutathione S-transferase (as described above; see also Smith et al., Gene 67:31–40, 1988). The fusion protein, which should conform to a predicted size, can then be purified with glutathione-Sepharose beads, eluted with glutathione, cleaved with thrombin, if desired (at an engineered cleavage site), and purified to the degree necessary for immunization of rabbits or mice.

Primary immunizations are typically carried out in Freund's complete adjuvant, and subsequent immunizations ("boosters") administered with Freund's incomplete adjuvant. Antibody titres are monitored by Western blot and immunoprecipitation analyses using the receptor protein fragment of the AZ3B-GST fusion protein. Immune sera are affinity purified using CNBr-Sepharose-coupled receptor proteins. The specificity of the antiserum can be determined using a panel of unrelated GST fusion proteins (such as GST-p53) and GST-trypsin (which may be generated by PCR using published sequences).

Alternatively, monoclonal antibodies may be prepared using the G protein-coupled receptor described herein, or a fragment thereof, and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerline et al., In Monoclonal Antibodies and T Cell Hybridomas, Elsevier, New York, N.Y., 1981). Once produced, monoclonal antibodies can be tested for their ability to specifically bind the G protein-coupled receptor by Western blot or immunoprecipitation analyses. Antibodies that specifically recognize the receptor of the invention are considered useful, for example, in determining the distribution of the receptor in various tissues, to assess therapeutic agents that specifically interact with the receptor, including the receptor's naturally occurring ligand, and to determine the relative state of differentiation of various cells that express the G protein-coupled receptor of the invention.

In addition to the intact monoclonal and polyclonal antibodies described above, the invention features various genetically engineered antibodies, humanized antibodies, and fragments of immunoglobulin molecules, such as Fab, Fab', (Fab')$_2$, Fv, and SCA fragments, that are capable of binding to an epitope of an AZ3B or AZ3B-like polypeptide. These antibody fragments, which retain some ability to selectively bind to the antigen (eg., an AZ3B antigen) of the antibody from which they are derived, can be made using well known methods in the art (see, eg., Harlow and Lane, supra), and are described further, as follows.

(1) A Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) A Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) A (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

In particular, the invention features "neutralizing" antibodies. By "neutralizing" antibodies is meant antibodies that interfere with any of the biological activities of the G protein-coupled receptor of the invention. These activities include, but are not limited to, induction of smooth muscle contraction, induction of histamine release, and increasing vascular permeability. Preferably, one or more of these activities will be reduced by at least 50%, more preferably by at least 70%, and most preferably by at least 90% or more. Preferably, the neutralizing antibody interferes with the interaction between the receptor and the ligand to which it naturally binds.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., Nature Genetics 7:13–21, 1994; see also U.S. Pat. Nos. 5,545,806 and 5,569,825, both of which are hereby incorporated by reference).

Skilled artisans can obtain guidance in preparing various antibodies or antibody fragments from the following publications. Ladner describes methods for preparing singly polypeptide chain antibodies (U.S. Pat. Nos. 4,946,778 and 4,704,692); Ward et al. describe the preparation of heavy chain variable domains, termed "single domain antibodies," which have high antigen-binding affinities (Nature 341:544–546, 1989); McCafferty et al., show that complete antibody V domains can be displayed on the surface of fd bacteriophage that specifically bind to antigen, and that rare phage (one in a million) can be isolated after affinity chromatography (Nature 348:552–554, 1990); Boss et al. describe various methods for producing immunoglobulins, and immunologically functional fragments thereof, which include at least the variable domain of the heavy and light chain in a single host cell (U.S. Pat. No. 4,816,397); and Cabilly et al. describe methods for preparing chimeric antibodies (U.S. Pat. No. 4,816,567).

Further, the antibody may be conjugated to an immunotoxin.

The members of a pair of molecules (e.g., an antibody-antigen pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

Use of the Nucleic Acids, Polypeptides, and Antibodies described above in the Diagnosis and Treatment of Inflammatory Diseases, Neurological Diseases, and Obesity It has been determined that C3a binds the receptor described herein (Crass et al., Eur. J. Immunol. 26:1944–1950, 1996; Ames et al. J. Biol. Chem. 271:20231–20234, 1996). C3a is released (along with C4a and C5a) early in the process of an inflammatory response, when the complement system is activated. These three molecules are potent pro-inflammatory molecules. They aid in the recruitment and activation of leukocytes, which eliminate foreign organisms and help maintain homeostasis. C3a is known to mediate a variety of inflammatory reactions, including smooth muscle contraction, increase in vascular permeability, chemotaxis of eosinophils, induction of the oxidative burst in neutrophils and eosinophils, and histamine release from IL-3 treated basophils and rat mast cells (for review, see Hugli, Curr. Top.

Microbiol. Immunol. 153:181, 1990; Kohl et al. (Eds.) Complement in Health and Disease, Kluwer Academic Publishers, Lancaster, 1993). In addition, a factor originally termed "acylation stimulating factor," which activates human adipocytes and skin fibroblasts, has been found to be C3a (Baldo et al., J. Clin Invest. 92:1543–1547, 1993; Cianflone et al., J. Biol. Chem. 264:426–430, 1989). This implies expression of the C3aR (i.e., the C3a receptor) in adipose tissue, and thus, a potential means of altering the response of these cells to C3a, which may in turn prove beneficial in treating obese individuals.

The relationship between the receptors of pro-inflammatory molecules, particularly the C3aR and the C5aR, as shown below in Table 2, was confirmed by Crass et al., who concluded that their experiment "identifies the C3aR as a G protein-coupled receptor and underlines its relatedness with the C5a and fMLP receptors."

Numerous ways of altering the expression or activity of the C3aR are known to skilled artisans. For example, living cells can be transfected in vivo with the nucleic acid molecules of the invention (or transfected in vitro and subsequently administered to the patient). For example, cells can be transfected with plasmid vectors by standard methods including, but not limited to, liposome- polybrene-, or DEAE dextran-mediated transfection (see, e.g., Felgner et al., Proc. Natl. Acad. Sci. USA 84:7413, 1987; Ono et al., Neurosci. Lett. 117:259, 1990; Brigham et al., Am. J. Med. Sci. 298:278, 1989), electroporation (Neumann et al., EMBO J. 7:841, 1980), calcium phosphate precipitation (Graham et al., Virology 52:456, 1973; Wigler et al., Cell 14:725, 1978; Felgner et al., supra) microinjection (Wolff et al., Science 247:1465, 1990), or velocity driven micro-projectiles ("biolistics"). These methods may be employed to mediate therapeutic application of the molecules of the invention. For example, antisense nucleic acids may be administered to inhibit gene transcription; without expression of the receptor itself, the C3a ligand, even if present in abundance, would not elicit the adverse reactions described above (e.g., contraction of smooth muscle and air passages, increased vascular permeability, and release of histamine). Methods of designing antisense nucleic acids and introducing them into host cells have been described in, for example, Weinberg et al. (U.S. Pat. No. 4,740,463; hereby incorporated by reference). Alternatively, nucleic acids can be administered so that expression of the receptor occurs in tissues where it is not normally expressed or is enhanced in tissues where it is normally expressed. This application can be used, for example, to stimulate phagocytosis (i.e., to enhance the infiltration of phagocytic cells into a tissue, such as a tumor). Preferably, the therapeutic nucleic acid (or recombinant nucleic acid construct) is applied to the site of the malignancy or inflammation, to the tissue in the larger vicinity of a malignancy or inflammation, or to the blood vessels supplying these areas.

Ideally, the production of AZ3B or similar G protein-coupled receptors (i.e., G protein-coupled receptors having an enlarged extracellular loop between the fourth and fifth extracellular domains) by any gene therapy approach described herein will result in a cellular level of receptor expression that is at least equivalent to the normal, cellular level of expression of these genes. Skilled artisans will recognize that these therapies can be used in combination with more traditional therapies, such as surgery, radiotherapy, or chemotherapy.

A further aspect of the invention is a method of treating a patient who has a disease or condition that is mediated by a G protein-coupled receptor having an enlarged extracellular loop between the fourth and fifth transmembrane domains. The method can be carried out by administering to the patient a reagent that modulates the activity of the receptor. Accordingly, the invention features therapeutic compositions that contain this reagent. As described herein, the reagent can consist of a nucleic acid, preferably an "antisense" nucleic acid, or of an antibody, including any of the antibody types described herein. Other useful reagents include molecules that bind to the receptor but do not transmit a signal across the cell membrane in which the receptor resides. The reagent can compete with the natural ligand of the receptor (and thereby reduce or prevent interaction between the receptor and the natural ligand), or it can interact with the natural ligand more directly, for example, as the ligand moves within the circulatory system, in such a way that the ligand does not bind the receptor as effectively as it otherwise would (in the absence of the reagent). The reagent may also modulate the activity of the receptor by altering the events that occur after the receptor is bound. For example, the reagent can alter the interaction between the receptor and the G protein with which it naturally interacts, or alter phosphorylation sites present in the intracellular domains of the receptor.

A disease or condition is said to be mediated by a receptor of the invention if the symptoms associated with it are caused by or exacerbated by binding of the receptor. The binding of the receptor need not be the initial or primary event in the development of the disease or condition. It is well within the abilities of skilled artisans to determine whether a disease or condition is mediated by a particular cellular event. The diseases that can be treated according to the method described above include inflammatory diseases such as asthma, chronic obstructive pulmonary disease, cystic fibrosis, sinusitis, rhinitis, atherosclerosis, glomerulonephritis, multiple sclerosis, and inflammatory bowel disease. The disease may also be a neurological disease, such as Alzheimer's disease. In addition, the method described above can be applied in the treatment of obesity. As described herein, the nucleic acids, polypeptides, and antibodies of the invention can also be used in the diagnosis of these diseases.

The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phosphoilpids, proteins (for example, serum albumin), EDTA, sodium chloride, liposomes, mannitol, sorbitol, and glycerol. The polypeptides or antibodies of the invention can be administered by any standard route of administration including intraperitoneal, intramuscular, subcutaneous, or intravenous administration. It is expected that the preferred route of administration will be intravenous.

It is well known in the medical arts that dosages for any one patient depend on many factors, including the general health, sex, weight, body surface area, and age of the patient, as well as the particular compound to be administered, the time and route of administration, and other drugs being administered concurrently.

Dosages for the polypeptides and antibodies of the invention will vary, but a preferred dosage for intravenous administration is approximately 0.01 mg to 100 mg/ml blood volume. Determination of the correct dosage within a given therapeutic regime is well within the abilities of one of ordinary skill in the art of pharmacology. Skilled artisans will be aided in their determination of an adequate dosage by previous studies. For example, Abraham et al. (J. Amer. Med. Assoc. 273:934–941, 1995) administered TNF-$\alpha$ monoclonal antibody (TNF-$\alpha$-MAb) at doses ranging from 1 to 15 mg/kg. The antibody was well tolerated by all patients, even though they developed human antimurine antibodies; no serum sickness-like reactions, adverse skin reactions, or systemic allergic reactions developed. Similarly, Rankin et al (Br. J. Rheumatol. 34:334–342, 1995) administered a single intravenous dose of 0.1, 1.0, or 10 mg/kg of an engineered human antibody, CDP571, which neutralizes human TNF-$\alpha$. Both studies describe in detail how to evaluate patients who have been treated with antibodies.

Identification and Administration of Compounds that Modulate the Activity of G Protein Coupled Receptors Having Enlarged Extracellular Domains Isolation of the nucleic acid molecules described above (i.e. those encoding a G protein-coupled receptor with an enlarged extracellular loop between the fourth and fifth extracellular domains) also facilitates the identification of compounds that can increase or decrease the expression of these gene in vivo. Many standard quantitative assays of gene expression can be utilized in this aspect of the invention. A few examples of these assays are provided below.

In order to identify compounds that modulate expression of AZ3B (or homologous genes) the candidate compound (which is either a pure compound or part of a mixture) can be added at varying concentrations to the culture medium of cells that express the receptor encoded by AZ3B (or its homologue). The expression of AZ3B is then measured, for example, by Northern blot analysis using a nucleic acid molecule of the invention as a probe. The formation of duplexes between the probe and the target sequences is described above. The level of AZ3B expression in the presence of the candidate molecule, compared with the level of expression in its absence, will indicate whether or not the candidate molecule effects the expression of AZ3B.

Alternatively, the effect of the candidate molecule may be assessed at the level of translation by measuring the level of AZ3B protein. This can be done, for example, by Western blot analysis or immunoprecipitation with an antibody that specifically binds the G protein-coupled receptor encoded by AZ3B.

If the modulatory compound is an inhibitory compound, it may function by competing with the ligand, C3a, for the limited number of receptors on the cell surface. These compounds may be identified by, for example, examining the binding of the ligand, C3a, to the receptor in the presence and absence of the candidate compound. A compound that disrupts the interaction that normally occurs between C3a and the G protein-coupled receptor of the invention may be especially useful in inhibiting the inflammation that occurs following activation of complement. Modulatory compounds that inhibit the expression or activity of the receptor can also reduce the severity or frequency of asthmatic reactions, chronic obstructive pulmonary diseases, bronchiectasis, sinusitis, rhinitis, cystic fibrosis, and inflammatory bowel diseases such as Crohn's Disease and ulcerative colitis.

The candidate modulatory molecules described above may be purified, substantially purified, or may remain as one component of a mixture of compounds (e.g., as an extract or a supernatant obtained from a cell culture). In an assay of mixed compounds, the expression of AZ3B (either at the mRNA or protein level) can be tested against progressively smaller subsets of the candidate compound pool. These subsets may be produced, for example, by standard purification techniques such as HPIC or FPLC, until a single compound or a minimal group of compound is demonstrated to modulate the expression of AZ3B.

Alternatively, or in addition, candidate modulatory compounds can be screened by assessing their ability to modulate one of the cellular events that occurs when the G protein-coupled receptor of the invention is bound by C3a. Examples of these events include the chemotaxis of eosinophils and the release of histamine from basophils or mast cells. The chemotactic activity or histamine release is simply compared in any standard assay in the presence and absence of the candidate compound.

Candidate modulatory compounds include polypeptide and non-polypeptide molecules, such as those found in cell extracts, mammalian serum, growth medium in which mammalian cells have been grown, or synthetic compounds. They also include nucleic acids that consists of AZ3B "antisense" sequence.

Modulatory compounds can be administered with a pharmaceutically acceptable diluent carrier, or excipient, according to conventional pharmaceutical practice, and any appropriate route of administration may be employed. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences.

Transgenic Animals

In another embodiment, the present invention relates to non-human, transgenic animals having cells that express a G protein-coupled receptor with an enlarged extracellular loop between the fourth and fifth transmembrane domains. Especially preferred are animals that express the receptor shown in FIG. 1. Such transgenic animals represent a model system for the study of conditions or diseases that are caused by or exacerbated by binding of the receptor, and for the development of therapeutic agents that modulate the activity of the receptor. The transgenic animals of the invention can be produced from animals which express the receptor of the invention or from "knock-out" animals that do not express the receptor. For example, knock-out mice, which do not express the murine homologue of the receptor encoded by AZ3B (SEQ ID NO:1), can be generated first, and animals from this line can be manipulated further to express the human homologue of the receptor (animals generated by "gene knock-out" are described further below). Expression of the human homologue may be directed to particular tissues or cell types through the use of tissue- or cell type-specific regulatory elements. Many such elements are known to skilled artisans.

In this context, the term "animal" denotes all mammals except Homo sapiens. Farm animals (pigs, goats, sheep, cows, horses, rabbits, and the like), rodents (such as rats, guinea pigs, and mice), and domestic animals (for example, dogs and cats) are within the scope of the present invention.

By "transgenic animal" is meant any animal containing cells that bear genetic information received, directly or indirectly, by deliberate genetic manipulation at the subcellular level, such as DNA received by microinjection or by infection with recombinant virus. Thus, animals of the invention are those with one or more cells that contain a recombinant DNA molecule. It is highly preferred that this molecule becomes integrated with the animal's chromosomes, but the use of DNA sequences that replicate extrachromosomally, such as might be engineered into yeast artificial chromosomes, is also contemplated.

The term "transgenic animal" also includes animals in which the genetic information has been taken up and integrated into a germ line cell. These animals typically have the ability to transfer the genetic information to their offspring. If the offspring in fact possess some or all of the genetic information delivered to the parent animal, then they, too, are transgenic animals.

Preferably, the transgenic animals of the present invention are produced by introducing DNA encoding the G protein-coupled receptor of the invention into single-celled embryos so that the DNA is stably integrated into the DNA of germ-line cells in the mature animal, and inherited in a Mendelian fashion. It has been possible for many years to introduce heterologous DNA into fertilized mammalian ova. For instance, totipotent or pluripotent stem cells can be transfected by microinjection, calcium phosphate-mediated precipitation, liposome fusion, retroviral infection, or other means. The transfected cells are then introduced into an embryo (for example, into the cavity of a blastula) and implanted into a pseudo-pregnant female that is capable of carrying the embryos to term. Alternatively, the transfected, fertilized ova can be implanted directly into the pseudopregnant female. In a preferred method, the appropriate DNA is injected into the pronucleus of embryos, at the single cell stage, and the embryos allowed to complete their development within a pseudopregnant female. These techniques are well known. For instance, reviews of standard laboratory procedures for microinjection of heterologous DNAs into fertilized, mammalian ova include: Hogan et al. "Manipulating the Mouse Embryo" (Cold Spring Harbor Press, Cold Spring Harbor, N.Y., 1986; Krimpenfort et al., Bio/Technology 9:86, 1991; Palmiter et al., Cell 41:343, 1985; Kraemer et al., "Genetic Manipulation of the Early Mammalian Embryo" (Cold Spring Harbor Press, Cold Spring Harbor, N.Y., 1985; Hammer et al., Nature 315:680, 1985; Purcel et al., Science, 244:1281, 1986; Wagner et al., U.S. Pat. No. 5,175,385; and Krimpenfort et al., U.S. Pat. No. 5,175,384 (the latter two publications are hereby incorporated by reference).

EXAMPLES

EXAMPLE I

The AZ3B cDNA Sequence and Predicted Amino Acid Sequence

A polypeptide that represents a new class of G protein-coupled receptors is described herein. It is encoded by a nucleic acid that was isolated from a human granulocyte cDNA library, as follows.

Isolation of the AZ3B cDNA Clone

A λgt11 cDNA library was prepared with MRNA from differentiated HL-60 granulocytes (Ye et al., Biochem. Biophys. Res. Commun. 180:105–111, 1991), and screened with a [$^{32}$P]-labeled probe consisting of 1.1 kb of a human FPR (N-formyl peptide receptor) cDNA (Boulay et al., Biochem. Biophys. Res. Commun. 168:1103–1109, 1990). Approximately 300,000 plaque forming units (pfus) were screened under the following conditions of stringency: hybridization at 62° C. with 6X SSC and 5X Denhardt's solution, followed by washing at the same temperature with 2X SSC.

A cDNA isolate was identified that appeared to hybridize weakly with the FPR cDNA probe. This isolate contained an insert of 1.45 kb and was named AZ7.4. The insert of AZ7.4 was sequenced according to the method described by Devereux et al. (Nucleic Acids Res. 12:387–395, 1984) and found to contain an open reading frame truncated at its 3' end with an EcoRi restriction site, presumably due to the incomplete methylation of the cDNA during library construction.

The same library was then screened again with the AZ7.4 DNA as a probe under comparable conditions of stringency, and three positive λ phage isolates were identified from 300,000 pfus. The isolate with the longest insert, AZ3B, was analyzed further by subcloning and sequencing.

Analysis of the AZ3B cDNA Sequence

The cDNA insert of AZ3B was 1970 base pairs long, and contained a 5' untranslated sequence of 81 base pairs, an open reading frame of 1446 bp, a stop codon, and a 3' untranslated sequence of 440 bp, including a stretch of 15 adenine bases (FIG. 1). The first ATG was assigned as the initiation codon based on the following criteria: (1) the flanking sequence meets the requirements for initiation of translation by eukaryotic ribosomes, namely a purine in position −3 and a guanine in position +4; (2) there is an in-frame stop codon at −10 to −12; and (3) the flanking sequence of the next ATG codon, 78 bp downstream, does not resemble the consensus sequence for translation initiation. The nucleotide sequence reported herein has been submitted to the GenBank/EMBL database and was assigned accession number U28488 (GenBank release 88).

The Amino Acid Sequence Encoded by AZ3B

Figure 3:
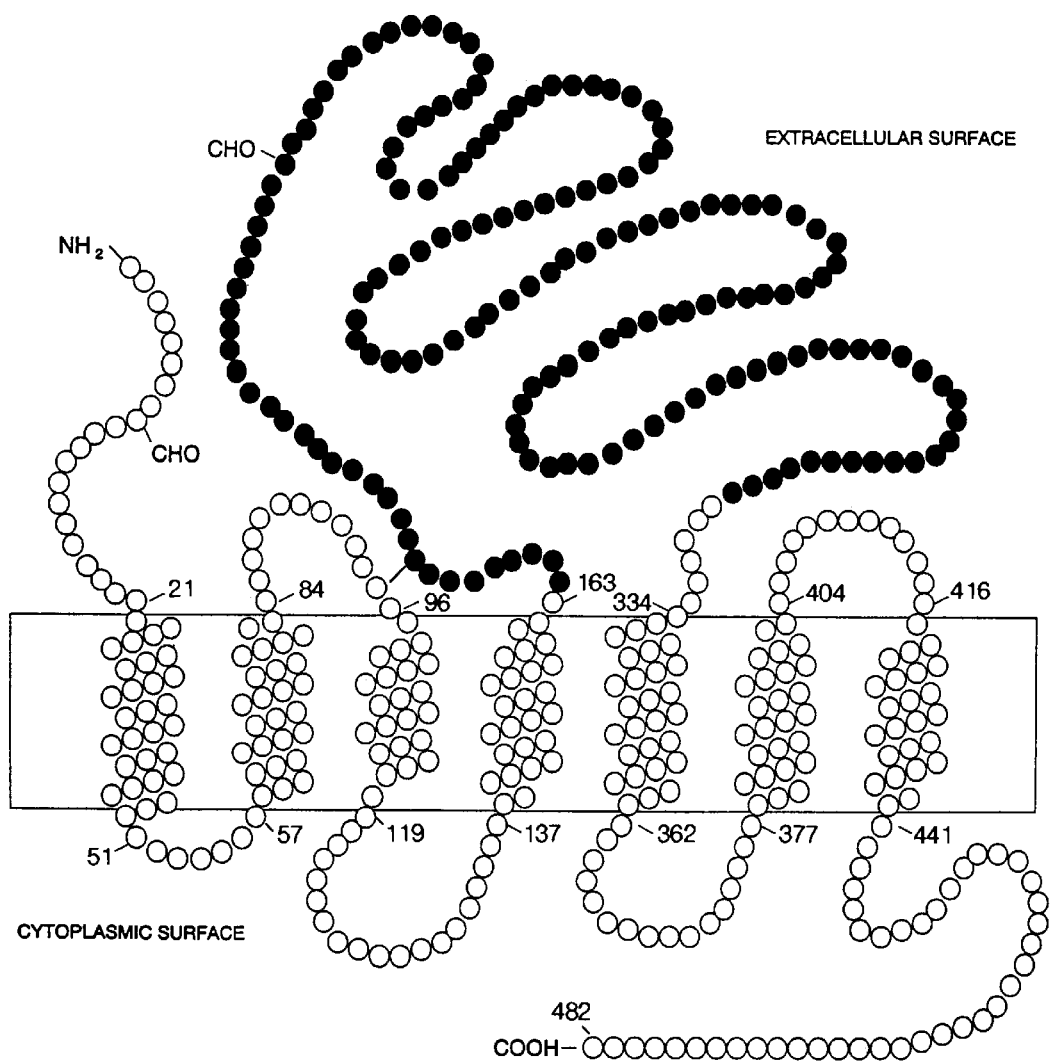
FIG. 3 is a diagram of the predicted disposition of the AZ3B protein in the cell membrane. Residues 164–327 (filled circles) denote sequence fused to the carboxyl termini of glutathione S-Transferase (GST) and maltose binding protein (MBP). Putative N-linked glycosylation sites are indicated by "CHO".

Based on the assignment of the first ATG codon, as described above, the open reading frame encodes a protein of 482 amino acids. Hydropathy analysis of the predicted protein product of AZ3B suggested the presence of seven putative transmembrane domains, a hallmark of the G protein-coupled receptors (FIG. 2). Unique to this putative receptor is the presence of an ~172-residue hydrophilic segment, which would form a large extracellular loop between the fourth and the fifth transmembrane domains (FIGS. 2 and 3). The sequence of this segment does not share significant homology with any protein in the GenBank (Release 88) or SWISS-PROT (Release 31) nucleic acid and protein sequence databases.

Analysis of the amino acid sequence identified two potential sites for N-linked glycosylation, one in the predicted large loop, and the other in the amino-terminus (FIG. 1). The deduced amino acid sequence of AZ3B was compared with all of the sequences in the SWISS-PROT database (Release 31), using the FASTA algorithm. The parameters of the search for related sequences were set so that gaps of up to 3 amino acids were allowed. The names of the most nearly identical sequences, all of which represent G protein-coupled receptors, are given in Table 1.

| SWISS-PORT Accession No. | GPCR Sequence Name | AZ3B/GPCR Sequences Compared (# of residues) | Identity |
|---|---|---|---|
| P21730 | Human C5a receptor | 22-163/36-177 (142) | 47.9% |
| P25090 | Human FPR homolog (FPR2) | 24-177/27-181 (155) | 44.5% |
| P30992 | Canine C5a receptor | 2-165/17-180 (164) | 43.9% |
| P30993 | Mouse C5a receptor | 10-177/20-189 (170) | 42.4% |
| P21462 | Human FPR | 24-177/27-181 (155) | 40.6% |
| P25089 | Human FPR homolog (FPRH2) | 9-178/11-182 (172) | 39.5% |
| P32303 | Frog type-a angiotensin II receptor | 28-177/34-186 (153) | 34.6% |
| Q04683 | Mouse Burkitt's lymphoma GPCR | 342–443/226-332 (107) | 34.6% |
| P25930 | Bovine NPY3 receptor | 24-173/40-188 (151) | 33.8% |
| P0938 | Rat somatostatin receptor-5 | 21-163/35-178 (144) | 32.6% |
| P32302 | Human Burkitt's lymphoma GPCR | 323-433/204-330 (127) | 32.3% |
| P25025 | Human IL-8 receptor B | 25-172/45-191 (150) | 31.3% |

As shown in Table 1, the deduced amino acid sequence of AZ3B is most nearly identical to the sequence of the human C5a receptor (47.9%). AZ3B is also 44.5% identical to an N-formyl peptide receptor (FPR) homologue, FPR2 (see Ye et al. Biochem. Biophys. Res. Commun. 184:582–589, 1991), and 40.6% identical to human FPR. The highest degree of sequence homology existed in a stretch of 170 residues in the amino terminus and in a 150 residue stretch in the carboxy terminus, with the exception of the Burkitt's lymphoma G protein-coupled receptor, where sequences in the sixth and seventh transmembrane domains and the third extracellular loop displayed the highest homology (Table 1). Once the ligand for the Burkitt's lymphoma G protein-coupled receptor is identified, it will become possible to determine whether the structural homology between this receptor and AZ3B reflects a similarity in ligand recognition.

The intracellular domains of AZ3B are also homologous to those of FPR and C5aR, suggesting that AZ3B is coupled to the same, or similar, G proteins as these receptors.

Despite the sequence homology, L cell fibroblasts that were transfected to express the AZ3B protein did not detectably bind the formyl peptide fMet-Leu-Phe or C5a; nor did these cells respond to fMet-Leu-Phe or C5a with calcium mobilization. In contrast, transfected cells expressing the FPR or C5aR bound fMet-Leu-Phe and C5a, respectively, and mobilized calcium in response. Other chemoattractants, including the platelet activating factor, MIP-1α, MCP-1, GROα, IL8, and I-309, also failed to stimulate measurable calcium mobilization in the AZ3B transfected cells.

Expression of AZ3B and Preparation of Antisera

Rabbit and mouse antisera were prepared against fusion proteins containing the large extracellular loop of AZ3B and glutathione S-Transferase (GST) and maltose binding protein (MBP), respectively (FIG. 3). More specifically, these antisera were raised against an expression protein that was obtained by inserting the AZ3B cDNA into the expression vector SFFV.neo (Fuhlbrigge et al., Proc. Natl. Acad. Sci. 85:5649–5653, 1988), and stably transfecting the mouse fibroblast cell line L2071 (available from the American Type Culture Collection, Rockville, Md.). The resultant cell line (L-AZ3) was shown to express the transfected protein by staining with polyclonal antibodies that were subsequently generated against fusion proteins containing a 164 residue stretch of the second extracellular loop of AZ3B.

EXAMPLE II

Analysis of AZ3B Expression Patterns
Analysis of AZ3B Distribution on the Cell Surface The expression of AZ3B protein on the cell surface was confirmed and further investigated by flow cytometry. The cell types analyzed included mouse L cells (untransfected and transfected with AZ3B), HL60 and U-937 cells (undifferentiated and differentiated, as described below), Molt 4/8 cells, H-9 cells, Raji cells, neutrophils and monocytes from peripheral blood, and endothelial cells collected from the umbilical vein, as shown in Table 2. The HL-α cells were differentiated with either dimethyl sulfoxide (DMSO, 13%, v/v) for 5 days, or dibutyryl cyclic AMP (500 μM) for 2 days. The U-937 cells were differentiated with phorbol myristate acetate (PMA; 0.1 μM) for 16 hours. The L cells were stably transfected to express the AZ3B protein. Cells were incubated with rabbit antisera or mouse antisera (indicated in Table 2 by *; at a 1:200 dilution) for 30 minutes on ice, then washed three times with PBS and incubated with FITC-conjugated goat anti-rabbit or anti-mouse secondary antibodies under the same conditions. In Table 2, the relative level of expression is indicated by the "−" and "+" signs.

| CELLS | EXPRESSION LEVELS |
|---|---|
| AZ3B-transfected mouse L cells | +++ |
| Untransfected mouse L cells | − |
| HL-60 | − |
| HL-60, DMSO differentiated | ++ |
| HL-60, dbcAMP differentiated | ++ |
| U-937 | + |
| U-937, PMA differentiated | +++ |
| Molt 4/8 | − |
| H-9 | − |
| Raji | +++ |
| Peripheral blood neutrophils | +++ |
| Peripheral blood monocytes* | +++ |
| Umbilical vein endothelial cells* | ++ |

As shown in Table 2, the expression of AZ3B protein is associated with terminal differentiation of several hematopoietic cell lines. AZ3B is also expressed at relatively high levels in neutrophils and monocytes, but is expressed at a low level in umbilical vein endothelial cells. The abundant expression of AZ3B protein in the Raji Burkitt Lymphoma cell line suggests that the function of AZ3B protein is not restricted to granulocytes.

Analysis of Az3B Tissue Distribution by Northern Blot

Figure 4A:
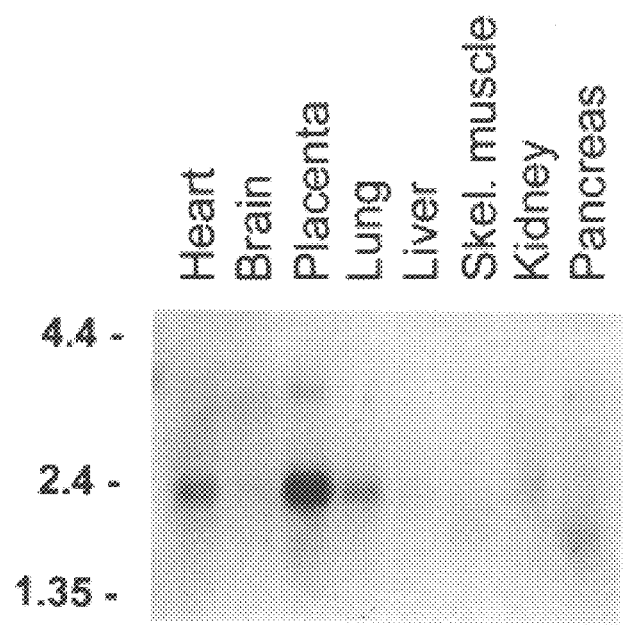
FIGS. 4A and 4B are photographs of Northern blots.
Figure 4B:
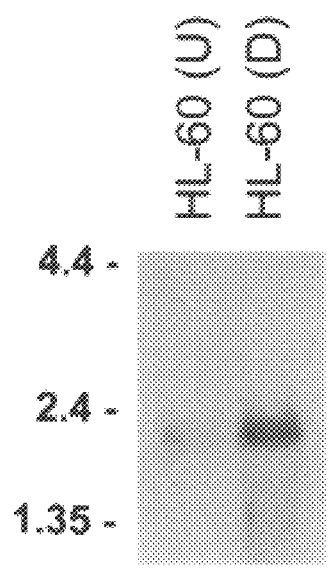

Further studies of AZ3B expression were carried out by Northern blot analyses to examine the distribution of this protein in various tissues (FIGS. 4A and 4B). Northern blot analysis was used to assess messenger RNA (mRNA) as follows. Poly(A)+RNA (2 μg) from eight different human tissues (heart, brain, placenta, lung, liver, skeletal muscle, kidney, and pancreas), was separated on a denaturing gel containing formaldehyde and 1.2% agarose, transferred to a nylon membrane by standard Northern blotting techniques, and fixed to the membrane by ultraviolet irradiation. The blot was prehybridized and hybridized in 50% formamide, 6X SSC, 25 mM HEPES (pH 7.0) and 1 mM EDTA, with dextran sulfate (10%). Hybridization was performed at 42° C. for 16 hours with a 1.5 kb AZ3B insert (truncated at the 3' end by digestion with EcoRI). Analysis of total RNA (20 µg) from undifferentiated ("U" in FIG. 4B) and differentiated ("D" in FIG. 4B) HL-60 cells was also performed, essentially as described above. To ensure that an equivalent amount of each sample was present, 28S and 18S RNA was stained.

These experiments also showed that the expression of AZ3B is induced in differentiated HL-60 cells. Furthermore, the AZ3B message was found in human heart, placenta, and lung. In the placenta, a second species of ~3.3 kb was seen in addition to the ~2.1 kb message found in other cells and tissues described above. This minor species may represent a different gene or a product of differential splicing.

The studies described herein indicate that the protein product of AZ3B is a G protein-coupled receptor that possesses a unique structural feature; an extracellular loop representing one third of the total receptor. The hydrophilicity of this loop implies that it can interact with a peptide or glycoprotein ligand, which remains to be identified.

What is claimed is:

1. An isolated nucleic acid sequence encoding the G-protein coupled receptor of SEQ ID NO:2.

2. The nucleic acid of claim 1, wherein the nucleic acid is mammalian.

3. The nucleic acid of claim 2, wherein the nucleic acid is human.

4. The isolated nucleic acid of claim 1, wherein "U" is substituted for all "T"s.

5. An expression vector comprising the nucleic acid of claim 1.

6. The expression vector of claim 5, further comprising a regulatory element.

7. The expression vector of claim 6, wherein the regulatory element directs tissue-specific expression.

8. The expression vector of claim 5, further comprising a reporter gene.

9. The expression vector of claim 8, wherein the reporter gene is selected from the group consisting of β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT).

10. The expression vector of claim 5, wherein the vector is a plasmid.

11. The expression vector of claim 5, wherein the vector is a virus.

12. The expression vector of claim 11, wherein the virus is a retrovirus.

13. An isolated cell comprising the vector of claim 5.

14. The cell of claim 13, wherein the cell is eukaryotic.

15. The cell of claim 13, wherein the cell is a fibroblast.

16. An isolated nucleic acid sequence encoding amino acid residues 163 to 327 of the G-protein coupled receptor of SEQ ID NO:2.

17. A method of producing a G protein-coupled receptor having an enlarged extracellular loop between the fourth and fifth transmembrane domains, the method comprising culturing the cell of claim 13 under conditions that allow expression of the receptor.

* * * * *

SEQUENCE LISTING

```
<160> NUMBER OF SEQ ID NOS: 2

<210> SEQ ID NO 1
<211> LENGTH: 1970
<212> TYPE: DNA
<213> ORGANISM: Human
<220> FEATURE:
<221> NAME/KEY: CDS
<222> LOCATION: (82)..(1527)

<400> SEQUENCE: 1
cggtggggac cagacaggac tcgtggagac atccaggtgc tgaagccttc agctactgtc      60
tcagtttttt gaagtttagc a atg gcg tct ttc tct gct gag acc aat tca     111
                        Met Ala Ser Phe Ser Ala Glu Thr Asn Ser
                          1               5                  10 act gac cta ctc tca cag cca tgg aat gag ccc cca gta att ctc tcc     159
Thr Asp Leu Leu Ser Gln Pro Trp Asn Glu Pro Pro Val Ile Leu Ser
             15                  20                  25 atg gtc att ctc agc ctt act ttt tta ctg gga ttg cca ggc aat ggg     207
Met Val Ile Leu Ser Leu Thr Phe Leu Leu Gly Leu Pro Gly Asn Gly
         30                  35                  40 ctg gtg ctg tgg gtg gct ggc ctg aag atg cag cgg aca gtg aac aca     255
Leu Val Leu Trp Val Ala Gly Leu Lys Met Gln Arg Thr Val Asn Thr
     45                  50                  55 att tgg ttc ctc cac ctc acc ttg gcg gac ctc ctc tgc tgc ctc tcc     303
Ile Trp Phe Leu His Leu Thr Leu Ala Asp Leu Leu Cys Cys Leu Ser
 60                  65                  70 ttg ccc ttc tcg ctg gct cac ttg gct ctc cag gga cag tgg ccc tac     351
Leu Pro Phe Ser Leu Ala His Leu Ala Leu Gln Gly Gln Trp Pro Tyr
75                  80                  85                  90 ggc agg ttc cta tgc aag ctc atc ccc tcc atc att gtc ctc aac atg     399
Gly Arg Phe Leu Cys Lys Leu Ile Pro Ser Ile Ile Val Leu Asn Met
                 95                 100                 105 ttt gcc agt gtc ttc ctg ctt act gcc att agc ctg gat cgc tgt ctt     447
Phe Ala Ser Val Phe Leu Leu Thr Ala Ile Ser Leu Asp Arg Cys Leu
            110                 115                 120 gtg gta ttc aag cca atc tgg tgt cag aat cat cgc aat gta ggg atg     495
Val Val Phe Lys Pro Ile Trp Cys Gln Asn His Arg Asn Val Gly Met
        125                 130                 135 gcc tgc tct atc tgt gga tgt atc tgg gtg gtg gct ttt gtg atg tgc     543
Ala Cys Ser Ile Cys Gly Cys Ile Trp Val Val Ala Phe Val Met Cys
    140                 145                 150 att cct gtg ttc gtg tac cgg gaa atc ttc act aca gac aac cat aat     591
Ile Pro Val Phe Val Tyr Arg Glu Ile Phe Thr Thr Asp Asn His Asn
155                 160                 165                 170 aga tgt ggc tac aaa ttt ggt ctc tcc agc tca tta gat tat cca gac     639
Arg Cys Gly Tyr Lys Phe Gly Leu Ser Ser Ser Leu Asp Tyr Pro Asp
```

```
                    175                 180                    185
ttt tat gga gat cca cta gaa aac agg tct ctt gaa aac att gtt cag         687
Phe Tyr Gly Asp Pro Leu Glu Asn Arg Ser Leu Glu Asn Ile Val Gln
                190                 195                 200 cgg cct gga gaa atg aat gat agg tta gat cct tcc tct ttc caa aca         735
Arg Pro Gly Glu Met Asn Asp Arg Leu Asp Pro Ser Ser Phe Gln Thr
            205                 210                 215 aat gat cat cct tgg aca gtc ccc act gtc ttc caa cct caa aca ttt         783
Asn Asp His Pro Trp Thr Val Pro Thr Val Phe Gln Pro Gln Thr Phe
        220                 225                 230 caa aga cct tct gca gat tca ctc cct agg ggt tct gct agg tta aca         831
Gln Arg Pro Ser Ala Asp Ser Leu Pro Arg Gly Ser Ala Arg Leu Thr
235                 240                 245                 250 agt caa aat ctg tat tct aat gta ttt aaa cct gct gat gtg gtc tca         879
Ser Gln Asn Leu Tyr Ser Asn Val Phe Lys Pro Ala Asp Val Val Ser
                255                 260                 265 cct aaa atc ccc agt ggg ttt cct att gaa gat cac gaa acc agc cca         927
Pro Lys Ile Pro Ser Gly Phe Pro Ile Glu Asp His Glu Thr Ser Pro
            270                 275                 280 ctg gat aac tct gat gct ttt ctc tct act cat tta aag ctg ttc cct         975
Leu Asp Asn Ser Asp Ala Phe Leu Ser Thr His Leu Lys Leu Phe Pro
        285                 290                 295 agc gct tct agc aat tcc ttc tac gag tct gag cta cca caa ggt ttc        1023
Ser Ala Ser Ser Asn Ser Phe Tyr Glu Ser Glu Leu Pro Gln Gly Phe
300                 305                 310 cag gat tat tac aat tta ggc caa ttc aca gat gac gat caa gtg cca        1071
Gln Asp Tyr Tyr Asn Leu Gly Gln Phe Thr Asp Asp Asp Gln Val Pro
315                 320                 325                 330 aca ccc ctc gtg gca ata acg atc act agg cta gtg gtg ggt ttc ctg        1119
Thr Pro Leu Val Ala Ile Thr Ile Thr Arg Leu Val Val Gly Phe Leu
                335                 340                 345 ctg ccc tct gtt atc atg ata gcc tgt tac agc ttc att gtc ttc cga        1167
Leu Pro Ser Val Ile Met Ile Ala Cys Tyr Ser Phe Ile Val Phe Arg
            350                 355                 360 atg caa agg ggc cgc ttc gcc aag tct cag agc aaa acc ttt cga gtg        1215
Met Gln Arg Gly Arg Phe Ala Lys Ser Gln Ser Lys Thr Phe Arg Val
        365                 370                 375 gcc gtg gtg gtg gtg gct gtc ttt ctt gtc tgc tgg act cca tac cac        1263
Ala Val Val Val Val Ala Val Phe Leu Val Cys Trp Thr Pro Tyr His
380                 385                 390 att ttt gga gtc ctg tca ttg ctt act gac cca gaa act ccc ttg ggg        1311
Ile Phe Gly Val Leu Ser Leu Leu Thr Asp Pro Glu Thr Pro Leu Gly
395                 400                 405                 410 aaa act ctg atg tcc tgg gat cat gta tgc att gct cta gca tct gcc        1359
Lys Thr Leu Met Ser Trp Asp His Val Cys Ile Ala Leu Ala Ser Ala
                415                 420                 425 aat agt tgc ttt aat ccc ttc ctt tat gcc ctc ttg ggg aaa gat ttt        1407
Asn Ser Cys Phe Asn Pro Phe Leu Tyr Ala Leu Leu Gly Lys Asp Phe
            430                 435                 440 agg aag aaa gca agg cag tcc att cag gga att ctg gag gca gcc ttc        1455
Arg Lys Lys Ala Arg Gln Ser Ile Gln Gly Ile Leu Glu Ala Ala Phe
        445                 450                 455 agt gag gag ctc aca cgt tcc acc cac tgt ccc tca aac aat gtc att        1503
Ser Glu Glu Leu Thr Arg Ser Thr His Cys Pro Ser Asn Asn Val Ile
460                 465                 470 tca gaa aga aat agt aca act gtg tgaaaatgtg gagcagccaa caagcagggg      1557
Ser Glu Arg Asn Ser Thr Thr Val
475                 480 ctcttaggca atcacatagt gaaagtttat aagaggatga agtgatatgg tgagcagcgg      1617
```

```
acttcaaaaa ctgtcaaaga atcaatccag cggttctcaa acggtacaca gactattgac    1677
atcagcatca cctagaaact tgttagaaat gcaaattctc aagccgcatc ccagacttgc    1737
tgaatcggaa tctctggggg ttgggaccca gcaagggcac ttaacaaacc ctcgtttctg    1797
attaatgcta aatgtaagaa tcattgtaaa cattagttct atttctatcc caaactaagc    1857
tatgtgaaat aagagaagct actttgtttt taaatgatgt tgaatatttg tcgatatttc    1917
catcattaaa ttttccttta gcattgtcta agtcttccaa aaaaaaaaaa aaa           1970
```

<210> SEQ ID NO 2
<211> LENGTH: 482
<212> TYPE: PRT
<213> ORGANISM: Human

<400> SEQUENCE: 2

```
Met Ala Ser Phe Ser Ala Glu Thr Asn Ser Thr Asp Leu Leu Ser Gln
 1               5                  10                  15

Pro Trp Asn Glu Pro Val Ile Leu Ser Met Val Ile Leu Ser Leu
            20                  25                  30

Thr Phe Leu Leu Gly Leu Pro Gly Asn Gly Leu Val Leu Trp Val Ala
        35                  40                  45

Gly Leu Lys Met Gln Arg Thr Val Asn Thr Ile Trp Phe Leu His Leu
    50                  55                  60

Thr Leu Ala Asp Leu Leu Cys Cys Leu Ser Leu Pro Phe Ser Leu Ala
65                  70                  75                  80

His Leu Ala Leu Gln Gly Gln Trp Pro Tyr Gly Arg Phe Leu Cys Lys
                85                  90                  95

Leu Ile Pro Ser Ile Ile Val Leu Asn Met Phe Ala Ser Val Phe Leu
            100                 105                 110

Leu Thr Ala Ile Ser Leu Asp Arg Cys Leu Val Val Phe Lys Pro Ile
        115                 120                 125

Trp Cys Gln Asn His Arg Asn Val Gly Met Ala Cys Ser Ile Cys Gly
    130                 135                 140

Cys Ile Trp Val Val Ala Phe Val Met Cys Ile Pro Val Phe Val Tyr
145                 150                 155                 160

Arg Glu Ile Phe Thr Thr Asp Asn His Asn Arg Cys Gly Tyr Lys Phe
                165                 170                 175

Gly Leu Ser Ser Ser Leu Asp Tyr Pro Asp Phe Tyr Gly Asp Pro Leu
            180                 185                 190

Glu Asn Arg Ser Leu Glu Asn Ile Val Gln Arg Pro Gly Glu Met Asn
        195                 200                 205

Asp Arg Leu Asp Pro Ser Ser Phe Gln Thr Asn Asp His Pro Trp Thr
    210                 215                 220

Val Pro Thr Val Phe Gln Pro Gln Thr Phe Gln Arg Pro Ser Ala Asp
225                 230                 235                 240

Ser Leu Pro Arg Gly Ser Ala Arg Leu Thr Ser Gln Asn Leu Tyr Ser
                245                 250                 255

Asn Val Phe Lys Pro Ala Asp Val Val Ser Pro Lys Ile Pro Ser Gly
            260                 265                 270

Phe Pro Ile Glu Asp His Glu Thr Ser Pro Leu Asp Asn Ser Asp Ala
        275                 280                 285

Phe Leu Ser Thr His Leu Lys Leu Phe Pro Ser Ala Ser Ser Asn Ser
    290                 295                 300

Phe Tyr Glu Ser Glu Leu Pro Gln Gly Phe Gln Asp Tyr Tyr Asn Leu
```

-continued

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |
| Gly | Gln | Phe | Thr | Asp | Asp | Gln | Val | Pro | Thr | Pro | Leu | Val | Ala | Ile |
|     |     |     |     | 325 |     |     |     |     | 330 |     |     |     |     | 335 |
| Thr | Ile | Thr | Arg | Leu | Val | Val | Gly | Phe | Leu | Leu | Pro | Ser | Val | Ile | Met |
|     |     |     |     | 340 |     |     |     |     | 345 |     |     |     |     | 350 |
| Ile | Ala | Cys | Tyr | Ser | Phe | Ile | Val | Phe | Arg | Met | Gln | Arg | Gly | Arg | Phe |
|     |     |     |     | 355 |     |     |     |     | 360 |     |     |     |     | 365 |
| Ala | Lys | Ser | Gln | Ser | Lys | Thr | Phe | Arg | Val | Ala | Val | Val | Val | Ala |
|     |     |     |     | 370 |     |     |     |     | 375 |     |     |     |     | 380 |
| Val | Phe | Leu | Val | Cys | Trp | Thr | Pro | Tyr | His | Ile | Phe | Gly | Val | Leu | Ser |
| 385 |     |     |     |     |     | 390 |     |     |     |     | 395 |     |     |     | 400 |
| Leu | Leu | Thr | Asp | Pro | Glu | Thr | Pro | Leu | Gly | Lys | Thr | Leu | Met | Ser | Trp |
|     |     |     |     | 405 |     |     |     |     | 410 |     |     |     |     | 415 |
| Asp | His | Val | Cys | Ile | Ala | Leu | Ala | Ser | Ala | Asn | Ser | Cys | Phe | Asn | Pro |
|     |     |     |     | 420 |     |     |     |     | 425 |     |     |     |     | 430 |
| Phe | Leu | Tyr | Ala | Leu | Leu | Gly | Lys | Asp | Phe | Arg | Lys | Lys | Ala | Arg | Gln |
|     |     |     |     | 435 |     |     |     |     | 440 |     |     |     |     | 445 |
| Ser | Ile | Gln | Gly | Ile | Leu | Glu | Ala | Ala | Phe | Ser | Glu | Glu | Leu | Thr | Arg |
|     |     |     |     | 450 |     |     |     |     | 455 |     |     |     |     | 460 |
| Ser | Thr | His | Cys | Pro | Ser | Asn | Asn | Val | Ile | Ser | Glu | Arg | Asn | Ser | Thr |
| 465 |     |     |     |     |     | 470 |     |     |     |     | 475 |     |     |     | 480 |
| Thr | Val |